United States Patent [19]

Hamaguri

[11] 4,266,554

[45] May 12, 1981

[54] DIGITAL OXIMETER

[75] Inventor: Kenji Hamaguri, Sakai, Japan

[73] Assignee: Minolta Camera Kabushiki Kaisha, Osaka, Japan

[21] Appl. No.: 50,097

[22] Filed: Jun. 19, 1979

[30] Foreign Application Priority Data

Jun. 22, 1978 [JP] Japan .................................. 53-76084

[51] Int. Cl.³ .............................................. A61B 5/00
[52] U.S. Cl. ...................................... 128/633; 356/41; 364/416
[58] Field of Search ............................... 128/633–635, 128/665–667; 356/39–41; 364/416–417

[56] References Cited

U.S. PATENT DOCUMENTS

| 3,677,648 | 7/1972 | Dorsch | 128/633 X |
| 3,787,124 | 1/1974 | Lowy et al. | 356/41 |
| 3,825,342 | 7/1974 | Lubbers et al. | 128/634 |
| 3,847,483 | 11/1974 | Shaw et al. | 128/634 |
| 3,948,248 | 4/1976 | Zuckerman et al. | 128/745 |
| 3,998,550 | 12/1976 | Konishi et al. | 128/633 X |
| 4,086,915 | 5/1978 | Kofsky et al. | 128/633 |
| 4,095,117 | 6/1978 | Nagy | 356/39 |
| 4,167,331 | 9/1979 | Nielsen | 128/633 |
| 4,213,462 | 7/1980 | Sato | 128/634 |

OTHER PUBLICATIONS

Tait, G. R. et al., "An Analog Computer for Ear Oximetry," Med. & Biol. Engr., vol. 5, pp. 463–472 1967.
Laing, R. A. "The Choroidal Eye Oximeter: An Instrument for Measuring Oxygen Saturation of Choroidal Blood In Vivo," IEEE BME Trans. vol. BME-22, No. 3, May, 1975, pp. 183–195.

Primary Examiner—Robert W. Michell
Assistant Examiner—Francis J. Jaworski
Attorney, Agent, or Firm—Jackson, Jones & Price

[57] ABSTRACT

A digital oximeter for noninvasively measuring oxygen saturation of the arterial blood is provided. Photoelectric transducers measure the light intensity after passing through living tissue to produce at least a pair of output signals of different wavelengths of light. A sample hold circuit is provided for correspondingly storing each of the respective output signals. A microprocessor controlled pulse activates a subsequent subtraction step between a second measurement taken for each of the respective wavelengths to correspondingly produce at least a first and second subtraction output. The circuit can then process at least the first and second stored light outputs and the first and second subtraction outputs to indicate the oxygen saturation.

5 Claims, 4 Drawing Figures

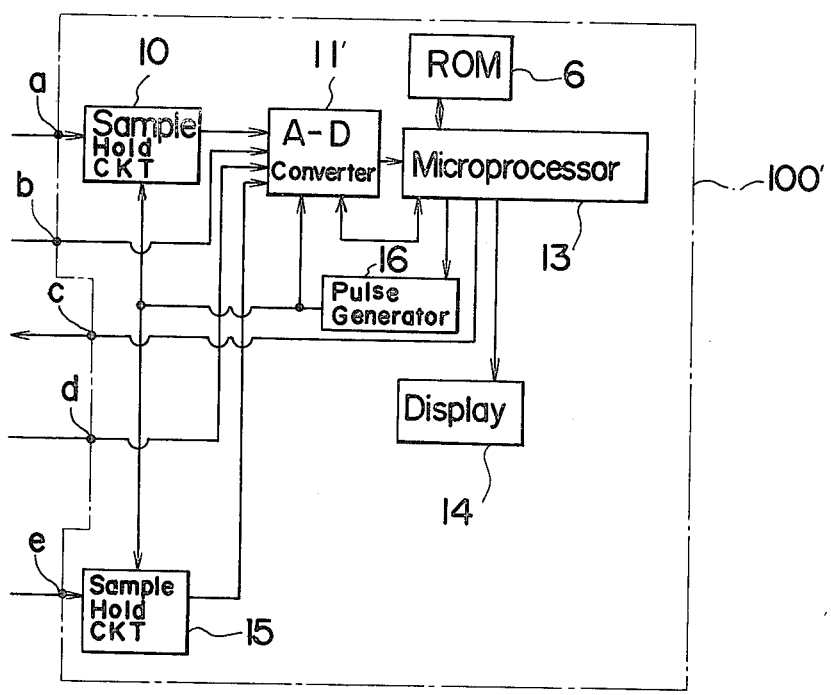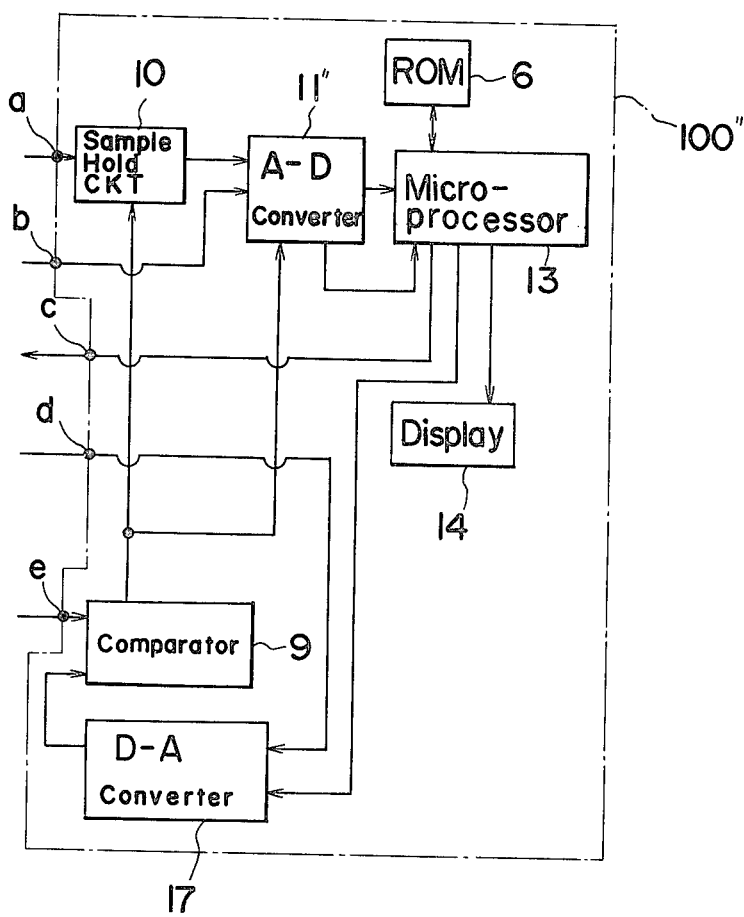

DIGITAL OXIMETER

BACKGROUND OF THE INVENTION

1. Field of the Invention

The present invention relates to a device for measuring the degree of oxygen saturation in blood and more particularly to a noninvasive oximeter capable of using a digital arithmetic processing circuit.

2. Description of the Prior Art

Noninvasive oximeters are well known and capable of calculating the degree of oxygen saturation from a light transmission factor at a measuring point on the human body, for example, the tip of a finger when the measuring point is exposed to light.

In general, methods for measuring oxygen saturation in arterial blood without penetrating body tissue utilize the relative difference between the light absorption coefficient of hemoglobin (Hb) and that of the hemoglobin oxide (HbO$_2$). The light absorption coefficient for Hb and HbO$_2$ is characteristically tied to the wavelength of the light traveling through them. Both Hb and HbO$_2$ transmit light having a wavelength in the infrared region to approximately the same degree. However, in the visible region, the light absorption coefficient for Hb is quite different from the light absorption coefficient of HbO$_2$.

Prior art noninvasive photoelectric type oximeters (referred to as "oximeter" hereinafter) can utilize teachings of a photoelectric plethysmograph. Changes in the light transmission factor of a measuring point such as the tip of a finger are caused by changes in the amount of blood contained in the tip of the finger, namely, the pulse rate, which occur due to variations in the amount of the arterial blood in the tip of the finger. In order to discriminate between oxidized hemoglobin and reduced hemoglobin, the oximeter employs two lights of different wavelengths and the collected transmitted lights are subjected to photoelectric conversion and then logarithmic conversion. The light absorbencies of the tip of a finger with respect to these lights are evaluated, and the periodically varying components of the signal are picked up for an appropriate arithmetic operation to eventually calculate the degree of oxygen saturation in the blood. However, if outputs from the photoelectric conversion are processed through analog circuitry, then the outputs are susceptible to changes in power supply voltage, room temperature, etc., and bear a low S/N (signal to noise) ratio, thus requiring a compensation technique.

In contrast to analog processing, a digital arithmetic circuit can be expected to avoid the above discussed problems. Nevertheless, application of a digital arithmetic circuit to an oximeter results in the following practical problems. At a measuring point such as the finger tip, light is absorbed mostly by bones, skin or other connecting tissues; absorption by blood is much less and the alternating current component of the light absorbancy, indicative of the absorption by blood, accounts for only a few percent of the total measured signal. Information must be extracted from such a slight amount of alternating current component to calculate the degree of oxygen saturation. If it is desired to detect as small as 1% of change in the degree of oxygen saturation, then approximately 4% of change in the alternating current component compared to the carrier signal should be sensed, thereby requiring a sensitivity in the order of up to four significant figures in measuring the transmission factor at the tip of a finger or the like. While the current photoelectric conversion technique can satisfy such a sensitivity or accuracy requirement, it is undesirable to employ digital processing which needs an arithmetic operation circuit having at least a capacity of four decimal digits or ten binary digits.

Cited of general interest are U.S. Pat. Nos. 3,998,550; 3,948,248; 3,677,648 and "The Choroidal Eye Oximeter: Instrument for Measuring Oxygen Saturation of Choroidal Blood In Vivo" by Laing et al; IEEE Transactions on Biomedical Engineering, Vol. BME-22, No. 3, May, 1975, pg. 183.

The prior art is still seeking improved accurate oximeters that can be economically manufactured.

SUMMARY OF THE INVENTION

It is, therefore, the object of the present invention to provide a digital oximeter which can monitor the degree of oxygen saturation with a reduced digit capacity for digital arithmetic operations through an improvement in calculation circuitry.

The present invention provides a digital oximeter for noninvasively measuring oxygen saturation of the arterial blood having transducers for measuring light intensity after contact with living tissue to produce at least a first light measuring output with respect to a first wavelength of light and a second light measuring output with respect to a second wavelength of light. Circuit means are provided for correspondingly storing each of the first and second light measuring outputs for a subsequent subtraction step between a second measurement of the first light measuring output from the first transducer and the first stored light measuring output from the storing means, and between a second measurement of the second light measuring output from the second transducer and the stored second light measuring output from the storing means to correspondingly produce at least first and second subtraction outputs, respectively. Finally, the circuit means processes at least the first and second stored light measuring outputs from the storing means and the first and second subtraction outputs from the subtraction practicing means to indicate the oxygen saturation.

BRIEF DESCRIPTION OF THE DRAWINGS

FIGS. 3 and 4 represent modifications of the FIG. 2 embodiment.

DETAILED DESCRIPTION OF THE PREFERRED EMBODIMENT

The following description is provided to enable any person skilled in the medical and electronic field to make and use the invention and sets forth the best mode contemplated by the inventor of carrying out his invention. Various modifications, however, will remain readily apparent to those skilled in the art since the generic principles of the present invention have been defined herein specifically to provide a relatively economical and easily manufactured noninvasive oximeter.

Figure 1:
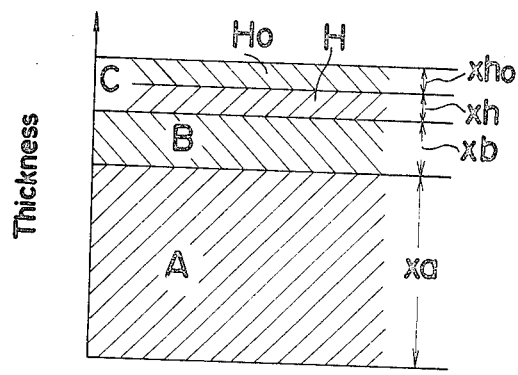
FIG. 1 is a cross-sectional view of a model representing a measuring position in the human body.

The operating principles of the present invention will be first described. An appropriate measuring point is illustrated in FIG. 1, by way of example, in which a layer of bone, skin or other organ or tissue rather than blood is schematically denoted as A, a layer consisting of venous blood as B and a layer of arterial blood as C. H represents the quantity of reduced hemoglobin contained therein and Ho represents the quantity of oxidized hemoglobin. The thicknesses of these respective layers are labeled Xa, Xb, Xh and Xho. If the intensity of incident light on the overall layers is denoted as Io, the intensity I of transmission light can be defined as follows:

$$I = I_o \cdot e^{-(Aa \cdot Xa + Ab \cdot Xb + Ah \cdot Xh + Aho \cdot Xho)}$$

wherein Aa, Ab, Ah and Aho are the light absorption coefficients of the respective layers.

(Aa·Xa+Ab·Xb) in the above defined formula shows a direct current component and (Ah·Xh+Aho·Xho) an alternating current component varying according to the pulse rate. If K denotes the constant portion of the exponential function in the above formula, the above formula can be rewritten as follows:

$$I_o = K \cdot I_o \cdot e^{-(Ah \cdot Xh + Aho \cdot Xho)} \quad (1)$$

The degree of oxygen saturation, S, sought to be evaluated can be defined as follows:

$$S = Xho/(Xh + Xho)$$

If $Xh + Xho = d$, then $$Xho = S \cdot d \text{ and } Xh = d \cdot (1 - S).$$

Therefore, the formula (1) can be rewritten:

$$I = K \cdot I_o \cdot e^{-[Ah \cdot (1-S) + Aho \cdot S] \cdot d} \quad (2)$$

In formula (2), d is a component variable with the progress of time and indicated in terms of d(t). If the transmission light at time $t_o$ is denoted as I, and that upon the expiration of a brief period of time, $\Delta t$, the transmitted light is denoted as I', then the latter can be written as follows because $I' = I + (dI/dt)\Delta t$ through a differentiation method:

$$\begin{aligned} I' &= I - [Ah \cdot (1 - S) + Aho \cdot S] \cdot K \cdot I_o \\ & \cdot e^{-[Ah \cdot (1-S) + Aho \cdot S]d} \cdot d'(t) \cdot \Delta t \\ &= I - I \cdot [Ah \cdot (1 - S) + Aho \cdot S] \cdot d'(t) \cdot \Delta t \end{aligned}$$

Therefore, $$\frac{I - I'}{I} = [Ah \cdot (1 - S) + Aho \cdot S] \cdot d'(t) \cdot \Delta t \quad (3)$$

wherein d'(t) is the differential coefficient of d(t).

$\Delta t$ in formula (3) is a controlled and known quantity, and the left side of the formula (3) can also be known by measuring the values of the transmission light, whereas S and d'(t) are the only unknown quantities, S being the intended value for evaluation.

An approach to delete the term d'(t) is suggested as follows. Two lights of different wavelengths $\lambda_1$ and $\lambda_2$ are employed, one wavelength $\lambda_1$ of the two wavelengths selected, shows a common absorption coefficient Ah' with respect to both reduced hemoglobin and oxidized hemoglobin while the other wavelength, $\lambda_2$, selected shows a different absorption coefficient Ah and Aho. The formula (3) with respect to the light of the wavelength $\lambda_1$ can be thus rewritten as follows:

$$\left(\frac{I - I'}{I}\right)_{\lambda_1} = Ah' \cdot d'(t) \cdot \Delta t \quad (4)$$

d'(t)$\Delta t$ can be evaluated from the above formula (4) and S can be therefore evaluated by substituting d'(t)$\Delta t$ into formula (3).

The foregoing sets forth the operating principle of measurement in the present invention, which is essentially identical with a method of evaluating S through logarithmical conversion of both sides of formula (2) and Fourier calculations, and can be regarded as an approximation based upon a differentiation method. The above summarized operating principle of the present invention is, however, of importance from a technical point of view when arithmetic operations are practically executed in accordance with the present invention, as will be fully understood from the following description.

First, the operating principle of the present invention eliminates the need to convert outputs via photoelectric conversion into logarithmical values. If logarithmic conversion is carried out in an analog fashion, then noise problems will be experienced because semiconductor devices have temperature and voltage sensitive characteristics and operate within a small current region. Contrarily, digital logarithmic conversion results in complexity of circuit construction and requires a capacity of more than ten digits for calculations. Nevertheless, pursuant to the teachings of the present invention, the numerators and denominators on the left sides of the formulas (3) and (4), the heart of the present invention, are similarly affected by changes in temperature and voltage. Strictly speaking, I and I' are taken at different points in time and thus are subject to different temperatures and different voltages, however, since $\Delta t$ is shorter than one period of the pulsation of the heart, changes in temperature, voltage, etc., are negligible, thereby eliminating measuring error. In addition, the major portions of I and I' in the left side of the formulas (3) and (4) are a direct current component unnecessary for arithmetic operations and completely eliminated by an operation of I-I', thus reducing correspondingly the necessary digit capacity for digital arithmetic operations. This, in turn, leads to a reduction in the number of necessary digits in performing digital calculations with respect to the right sides of formulas (3) and (4).

Figure 2:
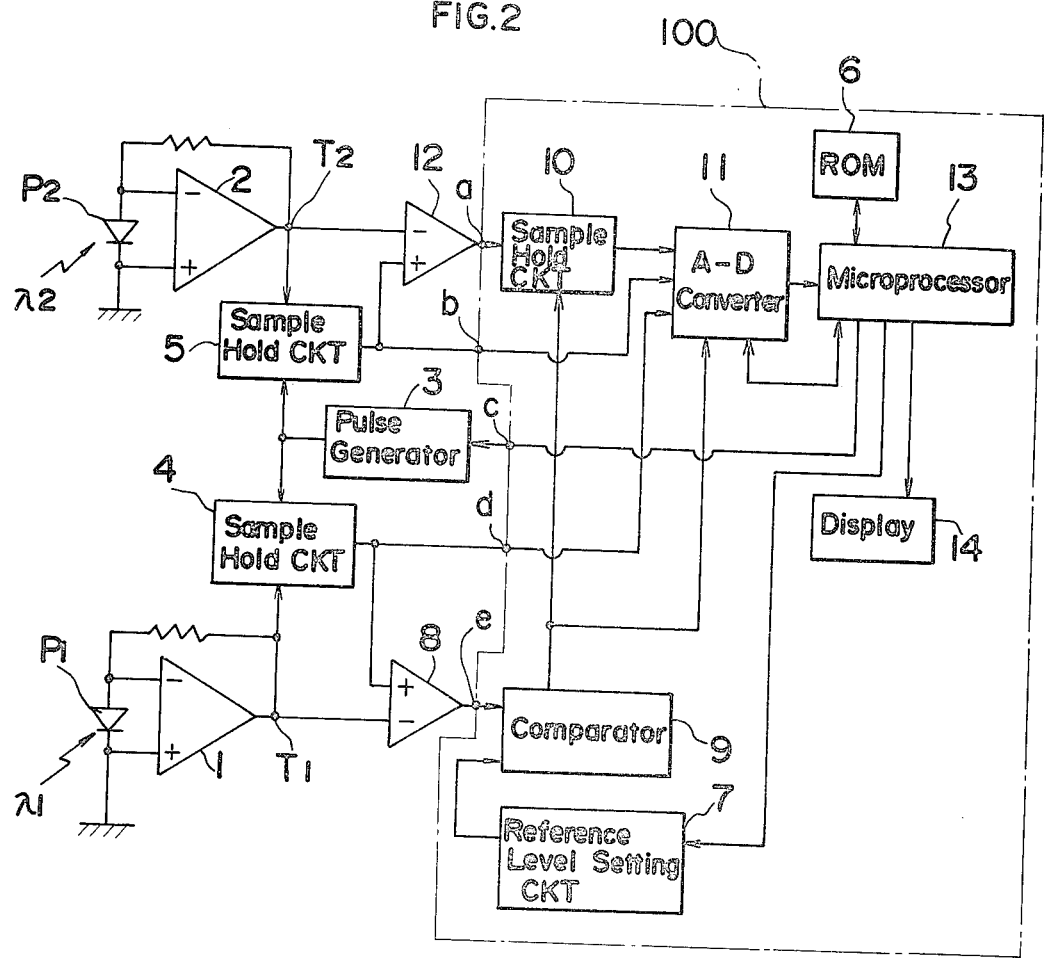
FIG. 2 is a block diagram of one preferred embodiment of the present invention.

The operating principle and the attendant features of the present invention have been described in the foregoing. In FIG. 2, there is provided a schematic representation of one preferred embodiment of the present invention. A pair of photoelectric transducers, e.g., photodiodes, P1 and P2 receive the transmission light through a measuring point of the human body. One of the transducers P1 receives light of the wavelength $\lambda_1$ and the other transducer P2 receives light of the wavelength $\lambda_2$. As stated above, the light of wavelength $\lambda_1$ shows the same absorption coefficients with respect to both reduced hemoglobin and oxidized hemoglobin, whereas the light of the wavelength $\lambda_2$ has a different absorption coefficient for both types of hemoglobin. Amplifiers 1 and 2 convert the photocurrent outputs from the transducers P1 and P2 into voltage signals and deliver the photoelectric conversion outputs (I and I' in the preceding formulas multiplied by an appropriate conversion coefficient) with respect to the lights of the wavelengths $\lambda_1$ and $\lambda_2$ from its output terminals T1 and T2. Sample hold circuits 4 and 5 sample and store the voltages at the terminals T1 and T2 in response to a pulse generated from a pulse generator 3. After the voltages are sampled and held upon development of a pulse, the output voltages stored within the sample hold circuits 4 and 5 and the next succeeding photoelectric conversion outputs appearing at the termals T1 and T2 are applied to subtraction circuits 8 and 12 so that signals corresponding to the numerators in the left sides of the formulas (3) and (4) are developed at the outputs of the subtraction circuits 8 and 12. The subtraction circuit 8 performs an arithmetic operation to provide the numerators as defined in formula (4), the output thereof being applied to a comparator 9 for comparison with a given reference level l from a reference level setting circuit 7. If the outputs from the subtraction circuit 8 and reference level setting circuit agree, the comparator 9 develops its output signal. The period of time extending between the development at the single pulse from the pulse generator 3 and the development of the output from the comparator 9 corresponds to Δt as defined in the formulas (3) and (4). The formula (4) can now be further defined as follows:

$$(I-I')\lambda_1 = Ah' \cdot d'(t) \cdot \Delta t \cdot (I)\lambda_1 = l'$$

wherein l' is l multiplied by a conversion coefficient associated with the photoelectric conversion or other conversion.

Therefore, $$d'(t) \cdot \Delta t = l'/Ah' \cdot (I)\lambda_1 \quad (5)$$

When the comparator 9 provides an agreement detection output, the sample hold circuit 10 samples and stores the instantaneous output from the subtraction circuit 12 which is defined as follows according to the formulas (3) and (5):

$$(I-I')\lambda_2 = [Ah \cdot (l-S) + Aho \cdot S] \cdot (l'/Ah') \cdot (I)\lambda_2/(I)\lambda_1 \quad (6)$$

An analog-to-digital converter 11 converts the analog signals stored within the sample hold circuits 4, 5 and 10 into digital signals individually. The analog signal in the sample hold circuit 10 is first converted in response to the output signals from the comparator 9. Upon the completion of this conversion, a timing pulse is transmitted from the A-D converter 11 to the microprocessor 13, which reads the output of the A-D converter 11 at this timing. Upon the completion of the reading, a timing signal is transmitted from the microprocessor 13 to the A-D converter 11 to initiate the A-D conversion of the output from the sample hold circuit 5. When this second conversion is completed, a timing signal is again transmitted from the A-D converter to the microprocessor 13, which reads the second conversion output. The output of sample hold circuit 4 is converted in the similar manner after the second conversion. Since the sample hold circuit 4 and 5 hold the values (I)λ1 and (I)λ2 as defined in the formulas (5) and (6), it is possible to evaluate S based upon the digital signals via the analog-to-digital converter 11 under the formula (6). A microprocessor 13 comprises a read only memory (ROM) 6 storing a program for execution of arithmetic operations. When information indicative of (l'/Ah') in the formula (6) is required during arithmetic operations, the voluntary value l' and the known absorption coefficient Ah' of the light of the wavelength λ1 by blood are stored within the ROM 6 or a read and write memory (RAM) not shown and, if necessary, retrieved therefrom for operations by the microprocessor. The level setting circuit 7 converts the value of l' read out from the ROM 6 or the like via the microprocessor 13 into analog voltage signals.

S is evaluated from the formula (6) as follows:

$$S = \frac{(I-I')\lambda_2 \cdot (I)\lambda_1}{(Aho-Ah) \cdot l'/Ah' \cdot (I)\lambda_2} - \frac{Ah}{Aho-Ah}$$

Since Ah and Aho in the above formula are known constants, $1/[Aho-Ah)(l'/Ah')] = A$ and $Ah$ $(Aho-Ah) = B$ are previously calculated and stored within the RAM, making it possible to evaluate the degree S of oxygen saturation under the following formula:

$$S = A \cdot (I-I')\lambda_2 \cdot (I)\lambda_1/(I)\lambda_2 - B$$

The resulting value S is displayed on a display 14. The value l' stored within the RAM is preselected such that Δt is considerably shorter than one period of the pulsation of the heart. The pulse generator 3 develops a single pulse pursuant to an instruction from the microprocessor 13. The analog-to-digital converter 11 converts sequentially the outputs of the sample hold circuits 4 and 5 into the corresponding digital signals shortly after the development of the pulse from the pulse generator 3, the timed relation thereof being governed by the microprocessor 13. After calculating the value S and sending it to the display 14, the microprocessor 13 instructs the pulse generator 3 to develop a new pulse for repeating the above detailed operation.

Above description is made with respect to the specialized case that the wavelength λ1 is selected to show a common absorption coefficient for both reduced hemoglobin and oxidized hemoglobin. However, this selection of the wavelength λ1 is only for the purpose of simplifying the formulae, and other selections of the wavelength λ1 are generally possible.

As a general case, formula (3) can be rewritten with respect to the wavelengths λ1 and λ2 as follows:

$$\left(\frac{I-I'}{I}\right)\lambda_1 = [(Ah)\lambda_1 \cdot (1-S) + (Aho)\lambda_1 \cdot S] \cdot d'(t) \cdot \Delta t \quad (7)$$

$$\left(\frac{I-I'}{I}\right)\lambda_2 = [(Ah)\lambda_2 \cdot (1-S) + (Aho)\lambda_2 \cdot S] \cdot d'(t) \cdot \Delta t \quad (8)$$

wherein (Ah)λ1 and (Aho)λ1 represent the absorption coefficients for reduced hemoglobin and oxidized hemoglobin with respect to the wavelength λ1, and (Ah)λ2 and (Aho)λ2 are similarly for the wavelength λ2.

From formula (7), $$(I-I')\lambda_1 = [(Ah)\lambda_1 \cdot (l-S) + (Aho)\lambda_1 \cdot S] \cdot d'(t) \cdot \Delta t \cdot (I)\lambda_1 = l''$$

$$d'(t) \cdot \Delta t = l''/[(Ah)\lambda_1 \cdot (l-S) + (Aho)\lambda_1 \cdot S] \cdot (I)\lambda_1 \quad (9)$$

From formulae (8) and (9), $$(I-I')\lambda_2 = \frac{[(Ah)\lambda_2 \cdot (1-S) + (Aho)\lambda_2 \cdot S] \cdot (I)\lambda_2 \cdot l''}{[(Ah)\lambda_1 \cdot (1-S) + (Aho)\lambda_1 \cdot S] \cdot (I)\lambda_1} \quad (10)$$

Above formula (10) may be substituted for formula (6) in the above general case, and S can be evaluated from formula (10).

As is apparent from the above disclosure, the present invention is characterized by light measuring circuits for different wavelengths having output terminals T1 and T2, sample hold circuits 4 and 5 correspondingly connected to the light measuring circuits, and subtraction circuits 8 and 12 correspondingly connected between the light measuring circuits and sample hold circuits. The outputs b and d from sample hold circuits 5 and 4 and the outputs a and e from the subtraction circuits 12 and 8 are processed by processing means 100 enclosed by the chain line block in FIG. 2. With respect to the processing means 100, however, various modifications are possible and can be substituted for the processing means 100, as shown in FIGS. 3 and 4.

According to the present invention, S is obtainable if $(I-I')\lambda_1$, $(I)\lambda_1$, $(I-I')\lambda_2$ and $(I)\lambda_2$ are obtained. These values are obtained at terminals e, d, a and b, respectively. Thus, the function required by the processing means 100 is only to perform a calculation to compute S. FIG. 3 shows a modified processing means 100', in which terminal e is connected to sample hold circuit 15 which is similar to sample hold circuit 10. Sample hold circuits 10 and 15 are responsive to a pulse from pulse generator 16 which is controlled by microprocessor 13. Microprocessor 13 actuates pulse generator 16 upon an expiration of a predetermined brief period of time $\Delta t$ after the actuation of pulse generator 3. Outputs from sample hold circuits 4, 5, 10 and 15, which correspond to $(I)\lambda_1$, $(I)\lambda_2$, $(I-I')\lambda_2$ and $(I-I)\lambda_1$, respectively are individually and successively converted into digital signals by A-D converter 11' under the control of the signal from pulse generator 16 and the timing signals reciprocating between A-D converter 11' and the microprocessor 13, and digitally calculated by microprocessor 13.

FIG. 4 shows another modification 100'' of the processing means, in which the reference level for comparator 9 is set by D-A converter 17 which is responsive to the output at terminal d. Sample hold circuit 10 holds the output from subtraction circuit 12 when comparator 9 produces the agreement detection output as in the case of FIG. 2. The outputs from sample hold circuits 5 and 10 are input to A-D converter 11'' and substantial calculation utilizing the outputs at terminals a, b, d and e is thus completed at A-D converter 11''.

In case of FIG. 4, the details of the function of processing means 100'' is as follows. D-A converter 17 produces, at its analog output, the reference level E according to the following relationship:

$$E = \gamma \cdot \alpha \cdot (I)\lambda_1 \quad (11)$$

wherein $\alpha$ is a digital signal from microprocessor 13 to be given at the digital input of the D-A converter, $\gamma$ is a constant inherent in D-A converter and $(I)\lambda_1$, is an output at terminal d, which is from sample hold circuit 4, to be the analog reference voltage of the D-A converter. From formula (7), output at terminal e from subtraction circuit 8 is represented as follows:

$$(I-I')\lambda_1 = (I)\lambda_1 \cdot [(Ah)\lambda_1 \cdot (I-S) + (Aho)\lambda_1 \cdot S] \cdot d'(t) \cdot \Delta t \quad (12)$$

Comparator 9 produces the agreement detection output when the following relationship exists:

$$G_1 \cdot (I-I')\lambda_1 = E \quad (13)$$

wherein $G_1$ is the gain of the subtraction circuit 8, which is practically a differential amplifier.

From formulae (11), (12) and (13), $$(I)\lambda_1 \cdot [(Ah)\lambda_1 \cdot (I-S) + (Aho)\lambda_1 \cdot S] \cdot d'(t) \cdot \Delta t = \gamma \cdot \alpha \cdot (I)\lambda_1 / G_1 \quad (14)$$

Therefore, the time $\Delta t$ determined by the comparator 9 is represented as follows:

$$\Delta t = \frac{\gamma \cdot \alpha}{G_1 \cdot [(Ah)\lambda_1 \cdot (1-S) + (Aho)\lambda_1 \cdot S] \cdot d'(t)} \quad (15)$$

On the other hand, the output to be stored in the sample hold circuit 10 is represented as follows in view of formula (8):

$$(I-I')\lambda_2 = (I)\lambda_2 \cdot [(Ah)\lambda_2 \cdot (I-S) + (Aho)\lambda_2 \cdot S] \cdot d'(t) \cdot \Delta t \quad (16)$$

Since $\Delta t$ in formula (16) is determined by formula (15), formula (16) is rewritten as follows:

$$(I-I')\lambda_2 = \frac{(I)\lambda_2 \cdot [(Ah)\lambda_2 \cdot (1-S) + (Aho)\lambda_2 \cdot S] \cdot \gamma \cdot \alpha}{G_1 \cdot [(Ah)\lambda_1 \cdot (1-S) + (Aho)\lambda_1 \cdot S]} \quad (17)$$

A-D converter 11'', into which the outputs of sample hold circuits 5 and 10 are input, produces a digital output, q, according to the following relationship since $(I-I')\lambda_2$ and $(I)\lambda_2$ are to be the analog input voltage and the analog reference voltage, respectively.

$$q = \frac{G_2 \cdot \beta \cdot (I-I')\lambda_2}{(I)\lambda_2} \quad (18)$$

wherein $G_2$ is the gain of the subtraction circuit 12, which is practically a differential amplifier, and $\beta$ is a constant inherent in A-D converter 11''. In view of formula (17), formula (18) can be rewritten as follows:

$$q = \frac{[(Ah)\lambda_2 \cdot (1-S) + (Aho)\lambda_2 \cdot S] \cdot \alpha \cdot \beta \cdot \gamma \cdot G_2}{[(Ah)\lambda_1 \cdot (1-S) + (Aho)\lambda_1 \cdot S] \cdot G_1} \quad (19)$$

In formula (19), $(Ah)\lambda_1$, $(Aho)\lambda_1$, $(Ah)\lambda_2$, $(Aho)\lambda_2$, $\alpha$, $\beta$, $\gamma$, $G_1$ and $G_2$ are known and q can be obtained as the output of the A-D converter 11''. This q is read when a conversion completion signal is transmitted from 11'' to 13. Therefore, S can be generally calculated by the microprocessor 13 according to formula (19).

In a specialized case of $(Ah)\lambda_1 = (Aho)\lambda_1$, formula (19) is simplified as follows:

$$S = \frac{G_1 \cdot (Ah)\lambda_1}{\alpha \cdot \beta \cdot \gamma \cdot G_2 \cdot [(Ah)\lambda_2 - (Aho)\lambda_2]} q - \frac{(Ah)\lambda_2}{(Ah)\lambda_2 - (Aho)\lambda_2} \quad (20)$$

In this case, S can be calculated by the microprocessor as a linear function of q which is obtained from the A-D converter 11''.

In the above embodiments, a pair of wavelengths of light are utilized. However, the present invention should not be restricted to the use of two wavelengths of light, but can be applicable to the use of more than two wavelengths of light. In case of the use of more than two wavelengths of light, one or more sets of a light measuring circuit, a sample hold circuit and a subtraction circuit similar to the combination of elements $P_2$, 2, 5 and 12 in FIG. 12 are added according to the principle of the present invention and the processing means 100 is suitably modified.

While the above embodiments have been disclosed as the best mode presently contemplated by the inventors, it should be realized that these examples should not be interpreted as limiting, because artisans skilled in this field, once given the present teachings, can vary from these specific embodiments.

Accordingly, the scope of the present invention should be determined solely from the following claims in which I claim:

1. A digital oximeter for noninvasively measuring oxygen saturation of the arterial blood comprising:

means for measuring light intensity after contact with living tissue to produce at least first and second time-spaced signals representative of the intensity of measured light at a first wavelength and first and second time-spaced signals representative of the intensity of measured light at a second wavelength;

means for correspondingly storing each of said first signals;

means for practicing subtractions between said first and second time-spaced signals of a first wavelength, and between said first and second time-spaced signals of a second wavelength to correspondingly produce at least first and second subtraction outputs, respectively; and means for processing at least said first signals from the storing means and said first and second subtraction outputs from the subtraction practicing means to indicate the oxygen saturation.

2. The invention of claim 1 wherein the processing means comprises means for comparing the first subtraction output with a reference level, means for storing the second subtraction output when a predetermined relationship exists between the first subtraction output and the reference level, and means for calculating the stored second subtraction output along with said stored first signals.

3. The invention of claim 1 wherein the processing means comprises means for correspondingly storing each of the first and second subtraction outputs upon expiration of a predetermined brief time after the storage of said first signals, and means for calculating the stored first and second subtraction outputs along with the stored first signals.

4. The invention of claim 1 wherein the processing means comprises means for producing a reference level responsive to said stored first signals with respect to the first wavelength of light, means for comparing the first subtraction output with the reference level, means for storing the second subtraction output when a predetermined relationship exists between the first subtraction output and the reference level, and means for calculating the stored second subtraction output along with said stored first signal with respect to the second wavelength of light.

5. The invention of claim 1 wherein the first wavelength of light with respect to the light measuring means is selected to show a common light absorption coefficient for both the reduced hemoglobin and the oxidized hemoglobin, and the second wavelength of light to show different light absorption coefficients for the reduced hemoglobin and the oxidized hemoglobin.

* * * * *